United States Patent [19]

Janssen

[11] 4,399,691

[45] Aug. 23, 1983

[54] SHIVE ANALYZER

[76] Inventor: Wladimir Janssen, 1024 Blvd. Demers, Carigan, Quebec, Canada, J3L 1E9

[21] Appl. No.: 286,852

[22] Filed: Jul. 27, 1981

[51] Int. Cl.³ .......................................... G01N 15/06
[52] U.S. Cl. ...................................................... 73/63
[58] Field of Search ................. 73/63, 61 R; 162/198, 162/263

[56] References Cited

U.S. PATENT DOCUMENTS 3,893,334 7/1975 Williams ............................ 73/63 X

FOREIGN PATENT DOCUMENTS 1100128 1/1968 United Kingdom .................... 73/63

Primary Examiner—James J. Gill
Assistant Examiner—Joseph W. Roskos

[57] ABSTRACT

The shive analyzer is formed by a closed chamber having a conical outlet with a spherical segment forming a plug for the outlet and defining an annular slot. The relative position of the plug and the conical outlet are accurately adjustable and these elements are mounted for relative movement to open the slot from a preset adjusted position. The analyzer is adapted for continuous operation and is fed by a positive displacement pump that pumps pulp at a preset constant rate. A device senses a determined increase in the pressure and opens the slot by relative movement of the spherical segment relative to the conical outlet. Another device counts the number of times the predetermined pressure increase is reached within a preset period of time to provide an indication of the number of shives in the pulp.

5 Claims, 1 Drawing Figure

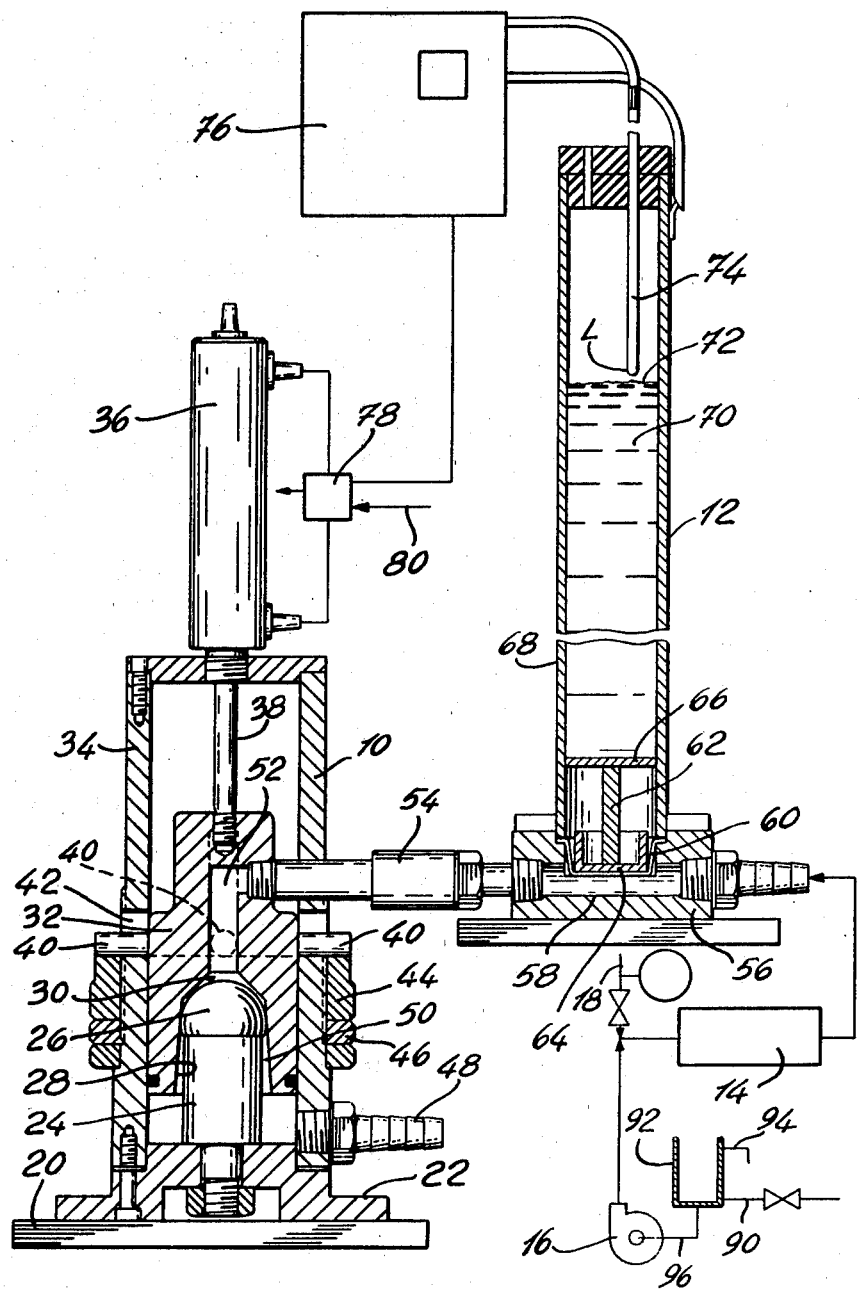

SHIVE ANALYZER

The present invention relates to a shive analyzer. More particularly the present invention relates to a slot type shive analyzer for continuously analyzing the shive content of a pulp.

There are many different methods practiced to determine the shive content of a pulp sample including; the blue sheet method wherein a pulp mat is dyed in such a manner that the shive are a different colour than the remainder of the sheet so that the number of shive may be counted; screening methods such as the English system using the Sumerville type screen, the Von Alfthan shive analyzer of which the present invention is an improvement and optical systems such as the optical system proposed by the Swedish Forest Products Research Laboratory which optically examines the pulp in suspension and determines the number of shives by sensing the change in light transmission through the sample and counting the number of changes.

The Von Alfthan shive analyzer comprises a tube generally made of glass that is freely suspended from its upper end so that it hangs vertically. The bottom end is formed as an outwardly flaring tapered outlet onto which a plug member having its upper end formed as a segment of a sphere is received so that a gap or slot is provided between the spherical plug and the tapered outlet. It will be apparent, since the tube is freely suspended, that any particles (shive) wedging into the slot may deflect the tube from its vertical position and thereby change the size of the slot i.e. deflect the tube to one side so that there is a larger slot on one side and a smaller slot or no slot on the other side and thereby impair significantly the accuracy of the instruments.

The Von Alfthan generally utilizes a long support means between the base and the upper suspending member from which the tube is suspended. This structure subjects the equipment to a further possibility of inaccuracy due to the differential in thermal expansion between the tube and the support member which can change the size of the slot with changes in the ambient temperature.

As above indicated the present invention is a slot type analyzer and is an improvement on the Von Alfthan analyzer described above and may be used on line in a pulp mill or substantially continuously.

Broadly the present invention relates to a shive analyzer comprising a closed chamber having a substantially conical outlet formed around a conical axis and a plug received in said conical outlet, said plug having substantially spherical segment at its end facing into said outlet and concentric with and adapted to cooperate with said conical outlet to defined annular slot centered on said conical axis of said conical outlet, means to accurately adjust the relative positions of said spherical segment end to said conical outlet along said conical axis thereby to adjust the width of said annular slot, means to substantially prohibit relative movement radial to said conical axis between said conical outlet and said plug, opening means for rapidly relatively moving said conical outlet and said spherical segment along said conical axis to open said slot from a preset position to an open position and return said conical outlet and spherical segment to said preset position, a passage leading to said closed chamber, means to deliver a pulp at a substantially constant flow rate through said passage into said closed chamber, means to sense a preset increase in pressure in said passage, means to trigger the opening means to relatively move said conical outlet and said spherical segment to said open position and immediately thereafter return same to said preset position each time said preset change in pressure is sensed, and means to count the number of times such triggering action occurs.

Further features, objects and advantages will be evident from the following detailed description of the preferred embodiments of the present invention taken in conjunction with the accompanying drawings in which:

The FIGURE is a partially schematic sectional view of the various parts of the present invention.

As shown the present invention comprises a closed stock outlet 10, a pressure sensor 12, if desired a static mixer 14, a positive displacement pump 16 for delivering pulp to the static mixer 14 and an adjustable water inlet line 18 for adjusting the consistency of the stock entering the mixer 14 or the pressure sensor 12 to insure that it is at a substantially constant preset consistency.

The stock outlet 10 is composed of a supporting frame generally indicated at 20 on which is mounted a base 22 which in turn mounts a plug member 24 having a closure forming end 26 in the form of a spherical segment.

The plug member 24 is axially aligned with the axis of conical outlet 28 (herein referred to as the conical axis) of a closed chamber 30 formed in a substantially cylindrical member 32. Cylindrical member 32 is slidably received within a tubular section 34 mounted on the base 22 for movement along the conical axis. A minimum tolerance is provided between the section 34 and the member 32 so that substantially no radial movement of the member 32 relative to the section 34 is permitted i.e. axial adjustment is permitted along the conical axis but the close fit between the section 34 and member 32 prohibits radial movement relative to the conical axis. Since the section 34 is fixed to the base 22 as is the plug member 24 the radial movement between the plug 24 and outlet 28 is substantially eliminated and the slot 50 formed between the plug 24 and outlet 28 will always be of substantially uniform width.

In the illustrated arrangement the member 32 is slidable in the tubular section 34 in a direction axially of the conical axis of the conical outlet 28 via a pneumatic cylinder arrangement 36 having a piston rod 38 connected to the member 32.

The movement of the member 32 axially within the tubular member 34 is controlled by diametrically opposed pins such as those illustrated at 40 that project through slots 42 in the wall of the tubular member 34. In the illustrated arrangement two such pins 40 and slots 42 are provided.

A micrometer nut 44 which threadably engages the outer diameter of the tubular member 34 provides a stop against which the pins 40 engage when the member 32 is at its preset position. A suitable lock nut 46 is used to lock the micrometer nut 44 in adjusted position.

Generally the member 32 should be short and have an overall length of about 4 to 5 inches so that the distance between the support pins 40 and plug 24 is short (less than about 6 inches) so that thermal expansion is not a problem. Also the member 32 and section 34 may have similar coeficient of expansion.

The tubular member 34 is provided with an outlet 48 for the pulp ejected through the annular metering slot 50 formed between the conical outlet 28 and the spherical segment 26 and concentric with the conical axis. This annular slot 50 which is adjusted by changing the position of the micrometer nut 44 provides the passage through which the pulp must pass. Any material having two dimensions larger than the width of the slot will be caught in this metering slot 50 and reduce the size of the outlet formed by this slot which will cause a build up a back pressure in a manner similar similar to the Von Alfthan shive analyzer. In the Von Alfthan because of the manner in which the tube is suspended the slot may be widened on one side and narrowed on the opposite side by radial deflection of the tube whereby control of slot size is lost and accuracy impaired. Such distortion of the slot 50 does not occur with the present invention.

The stock enters the chamber 30 via passage 52 which is connected to a pressure sensor 12 via a connecting pipe 54. In the illustrated arrangement the pressure sensor 12 comprises a base housing 56 having a pressure 58 therethrough and a pressure sensor projecting into the passage 58 and to sense the pressure in this passage and thereby the pressure in the chamber 32.

In the illustrated arrangement the pressure sensor is formed by a rolling diaphragm 60 (such as those sold by Bellofram Corporation, Burlington, Mass.) held in position via a guide 62 having a lower piston member 64 attached to the rolling diaphragm 60 to control the flexing of the diaphragm 60 in the conventional manner and an upper guide disk 66 received in and guided by the tubular member 68 to insure straight line movement of the guide 62.

This tubular member 68 is adapted to contain a fluid 70 and is filled to a predetermined level such as the level 72 to provide a preset pressure on the diaphram 60. A probe 74 is connected to suitable source of power, as is the housing 68, so that when the fluid 70 (generally water) reaches the level L at the lower end of the probe 74 (which level may be preadjusted) electrical contact is made which triggers the operation of the counter and actuater mechanism 76 which in turn controls the salenoid valve 78. Valve 78 diverts the air pressure in line 80 from upper end of the cylinder 36 to the lower end of the cylinder 36 while venting the top end thereby to lift the member 32 and increase the size of the annular slot 50 so that it will be cleaned and immediately thereafter to reverse the flow of air so that air flows to the top of the cylinder 36 and forces the member 36 back into position with the pins 40 in firm engagement with the micrometer nut 44.

The operation of the device will be self evident from the above however it will now be briefly described. Pulp from a suitable source is directed to the system via line 90 and into a reservoir 92 provided with an overflow 94 so that more pulp may enter the reservoir than is required by the pump 16 with the excess being returned to the pulping system via the overflow. The provision of the reservoir 92 also permits testing of discrete samples. Pulp is pumped from reservoir 92 via line 96 by the positive displacement pump 16 and flows at a predetermined constant rate of flow set in relation to the size of the slot 50, (for correlation with the Von Alfthan analyse the flow for a given slot size may be adjusted to obtain the flow to the chamber 30 as recommended for the Von Alfthan). This pulp is diluted with water from line 18 to adjust the consistency to that required (i.e. the consistency of the pulp before the pump 16 may be sensed and the required amount of water added) or alternatively the consistency may be adjusted before the pulp enters the pump 16. In any event a constant known rate of flow and consistency must be provided into the chamber 30. If desired a suitable mixer 14 may be provided. In the illustrated arrangement in line mixer 14 has been used to thoroughly mix the water with the pulp to ensure that the consistency of the pulp is substantially uniform. The pulp then passes through the passage 58 in the pressure sensor 12, passage 54, 52 and into the chamber 30 and issues out of the chamber 30 via the outlet slot 50 and is rejected from the system via the outlet 48. In this operation the cylinder 36 forces the pins 40 into tight engagement with the micrometer adjustment nut 44.

As the shives are trapped in the outlet slot 50 the flow of pulp from the chamber 30 is impeded which generates a back pressure on the line. This back pressure provides a pressure against the diaphram 60 tending to lift the liquid 70 in the tubular section 68. This movement raises the level 72 until it reaches the level L and triggers the counter actuating mechanism 76 to operate the solenoid operated air valve 80, which directs air pressure to the bottom of the cylinder 36, opens the passage formed by the annular slot 50 and immediately thereafter returns the member 32 to its initial position with the pins in firm engagement the micrometer nut 44 by redirecting the flow of air to the top of the cylinder 36.

The counter and actuator mechanism 76 counts the number of times the level L is reached in a preset time interval. This number gives an indication of the number of shive in the pulp sample.

While a water column has been shown as the pressure means any suitable accurate pressure sensor may be used to trigger the counter and actuator mechanism 76. Similarly the micrometer adjustment has been used on the outside of the tubular member 34 to adjust the axial position of the member 32, if desired the member 32 could remain stationary and the member 24 adjusted. However it is preferred to provide the micrometer nut on the outside of the tubular member 34 since this permits the maximum diameter for the threads which in turn permits greater accuracy.

Modifications may be made without departing from the spirit of the invention as defined in the appended claims.

I claim:

1. A shive analyzer comprising a closed chamber having a substantially conical outlet, a plug received within said conical outlet formed around a conical axis, said plug having a substantially spherical segment as its end facing into said outlet and concentric with and adapted to cooperate with said conical outlet to define an accurate annular outlet slot centred on said conical axis of said conical outlet, means to accurately adjust the relative positions of said spherical segment and said conical outlet along said conical axis thereby to adjust the width of said annular slot, said plug and said outlet being substantially free from relative radial movement with respect to one another and to said conical axis in order to maintain constant the relative position between said outlet and said spherical segment, opening means for rapidly relatively moving said conical outlet and said spherical segment along said conical axis to open said slot from a preset position to an open position and return said conical outlet and spherical segment to said preset position, a passage leading to said closed chamber, means to deliver a pulp at a substantially constant rate of flow through said passage into said closed chamber, means to sense a preset increase in the pressure in said passage, means to trigger said opening means to relatively move said conical outlet and said spherical segment to said open position and immediately thereafter return same to said preset position each time said preset increase in pressure is sensed and means to count the number of times such triggering action occurs.

2. A shive analyzer as defined in claim 1 wherein said conical chamber is formed within a cylindrical member which is slidably received for movement along said conical axis within a tubular section mounted on a base to which said plug is firmly secured, said cylindrical member and said tubular section permitting said cylindrical member to move along said conical axis while substantially preventing radial movement relative to said conical axis.

3. A shive analyzer as defined in claim 2 wherein said cylindrical member is support on said means to accurately adjust by supporting means contacting said means to accurately adjust, the distance between said supporting means and said plug being short so that thermal expansion of said tubular section and said cylindrical member does not materially effect the size of said slot.

4. A shive analyzer as defined in claim 1 wherein said closed chamber is formed within a sliding member mounted for movement relative to said plug, a micrometer adjustment means for adjusting the position of said sliding member relative to said plug, abutment means on said sliding member adopted to engage said micrometer adjustment means, said means for opening holding said abutment means in firm contact with said micrometer adjustment when said conical outlet and said spherical segment are in preset position.

5. A shive analyzer as defined in claims 1, 2, 3 or 4 wherein said means for sensing said pressure comprises a rolling diaphram forming one boundry of said passage, a hydraulic head on the opposite side of said reversible diaphram, movement of said rolling diaphram changing the height of said hydraulic head and providing an electrical contact after a predetermined change in said head, said electrical contact providing said means to trigger said opening means.

* * * * *